United States Patent

Bergthaller et al.

Patent Number: 4,546,073
Date of Patent: Oct. 8, 1985

[54] PHOTOGRAPHIC RECORDING MATERIAL CONTAINING A PRECURSOR OF A PHOTOGRAPHICALLY-ACTIVE COMPOUND

[75] Inventors: Peter Bergthaller, Cologne; Heinrich Odenwälder; Reinhard Matejec, both of Leverkusen, all of Fed. Rep. of Germany

[73] Assignee: Agfa-Gevaert Aktiengesellschaft, Leverkusen, Fed. Rep. of Germany

[21] Appl. No.: 610,786

[22] Filed: May 16, 1984

[30] Foreign Application Priority Data

May 28, 1983 [DE] Fed. Rep. of Germany ....... 3319428

[51] Int. Cl.[4] ............................................. G03C 7/26
[52] U.S. Cl. .................................. 430/543; 430/544; 430/553; 430/555; 430/557; 430/558; 430/559; 430/955; 430/957
[58] Field of Search ............... 430/553, 555, 557, 558, 430/559, 544, 543, 955, 957

[56] References Cited

U.S. PATENT DOCUMENTS

| | | | |
|---|---|---|---|
| 4,115,121 | 9/1978 | Evans et al. | 430/557 |
| 4,146,400 | 3/1979 | Lowski et al. | 430/557 |
| 4,438,193 | 3/1984 | Uemura et al. | 430/544 |
| 4,459,351 | 7/1984 | Adin et al. | 430/955 |

Primary Examiner—J. Travis Brown
Attorney, Agent, or Firm—Connolly and Hutz

[57] ABSTRACT

Precursor compounds from which photographically-active compounds are released with a time delay correspond to the following general formula

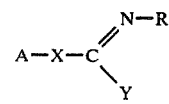

wherein
A represents the residue of a compound which undergoes oxidative coupling;
X represents —O—, —S— or —NR[1]—;
Y represents a releasable group which may consist of or contain the residue of a photographically-active compound; and
R represents a group for controlling the kinetics of release.

Advantageous pictorial properties (inter-image effect, edge effect, modulation transfer function) are obtained with compounds according to the present invention if the photographically-active residue is the residue of a development inhibitor.

4 Claims, No Drawings

PHOTOGRAPHIC RECORDING MATERIAL CONTAINING A PRECURSOR OF A PHOTOGRAPHICALLY-ACTIVE COMPOUND

This invention relates to a photographic recording material having at least one light-sensitive silver halide emulsion layer and containing at least one precursor of a photographically-active compound from which the photographically-active compound is released in imagewise distribution under the conditions of photographic development.

The imagewise release of photographically-active compounds has been known for a considerable time. This phenomenon is used, for example, in various dye diffusion transfer processes, in which a photographically-active compound, in this case a diffusible dye, is released in imagewise distribution from a dye-releasing compound as a result of the development of silver halide which has been exposed imagewise, and this photographically-active compound is transferred to an image receptor layer. The present invention relates to precursor compounds of the type in which the photographically-active compound is released imagewise as the result of an oxidative coupling reaction brought about by the development of silver halide which has been exposed imagewise. A dye diffusion transfer process based on such a reaction has been described, for example, in No. DE-C-1,095,115. In one variation of the process described here, the colour coupler compounds used contain a coloured molecule moiety in the coupling position and release this moiety as a diffusible dye when that part of the compound which is capable of coupling reacts with the oxidation product of a colour developer compound, namely a p-phenylene diamine compound. Instead of a dye residue, some other photographically-active compound may be released in this manner, e.g. a coupler, a hardener, a silver halide solvent, or some other compound capable of accelerating or retarding the reactions which take place in the course of development and processing of the photographic recording material. Compounds which have become particularly important in this respect are the so-called "DIR couplers". These are compounds which release a development inhibitor attached at the coupling position when coupling takes place (DIR=development inhibitor releasing). For information on DIR couplers, see U.S. Pat. No. 3,227,554. Photographically-active compounds may also be released from compounds which are capable of undergoing oxidative coupling under the conditions of photographic development without forming a dye as a result of coupling. Information on such compounds may be found, for example, in No. DE-C-1,547,640. The use of DIR couplers is important, for example, for producing various photographic effects, such as inter-image effects or influencing the gradation and improving the sharpness of the image [Photographic Science and Engineering 13, 74, (1969)].

A considerable further improvement may be achieved if the photographically-active compound does not become active immediately after the coupling reaction which releases the compound from the coupler, but only after a certain time delay. This means that the photographically-active compound or a precursor thereof is capable, by virtue of its diffusibility, of diffusing from its site of release into its surroundings for a certain period of time after its release from the coupler moiety before it becomes active. The photographically-active compound may become active as a result of a time controlled release of a so-called "time control member" to which the photographically-active compound is attached and which is itself attached to the coupler at the coupling position. Release of the photographically-active compound from the time control member takes place as a consequence of the time control member with the photographically-active compound attached thereto being released from the coupler. Precursor compounds of this type have been disclosed, for example, in No. DE-A-2,703,145; No. 2,855,697; No. 3,105,026 and No. 3,209,671. Known time control members thus include, for example, a group of the formula

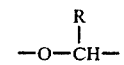

in which the oxygen atom is attached to the coupler at the coupling position and the carbon atoms is attached to a nitrogen atom of a photographically-active compound;

a group which undergoes an intramolecular nucleophilic displacement reaction after release from the coupler to make the photographically-active compound available; or a group in which electron transfer may take place along a conjugated system, whereby the photographically-active compound is released.

Although the known DIR couplers, with or without time control member, could be used to achieve a marked improvement in some of the important properties determining the image quality, there still exists need for new precursor compounds from which the photographically-active compounds may be released with a controlled time delay and which enable further improvements to be achieved in some of the important properties, such as the inter-image effects and edge effects. Precursor compounds having a new type of time control group have now been found.

The present invention relates to a photographic recording material having at least one silver halide emulsion layer, characterised by containing a compound corresponding to the following general formula I:

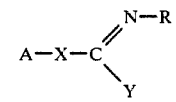

wherein

A represents the residue of a compound which is capable of oxidative coupling with a silver halide developer compound under the conditions of photographic development;

X represents —O—, —S— or —NR$^1$—;

Y represents a releasable group which is split off from C under the conditions of photographic development, carrying with it the bonding electron pair between C and Y, when X is split from A, carrying with it the bonding electron pair between A and X, and Y is preferably the residue of a photographically-active compound or the residue of a compound from which a photographically-active compound is formed under the conditions of photographic development;

R represents alkyl, aralkyl, aryl, acyl, a heterocyclic group or a group —NH—acyl, —OR$^2$, or —P(O)(OR$^2$)$_2$;

R$^1$ represents H, alkyl, aryl, alkylsulphonyl or arylsulphonyl; and

R$^2$ represents alkyl, aryl or a heterocyclic group.

A is preferably the residue of a colour coupler or the residue of a coupling compound which undergoes coupling substantially without producing a colour and the group

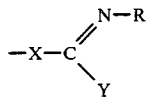

is bonded to the coupling position of A. The colour coupler A may be, for example, the residue of a conventional cyan coupler, magenta coupler or yellow coupler. Suitable structures of such couplers are well known. When A is the residue of a colour coupler, the compounds according to the present invention are generally 2-equivalent couplers, regardless of whether the releasable group Y does or does not represent or contain a photographically-active compound. The group A generally carries ballast groups to enable the precursor compounds according to the present invention to be incorporated in a diffusion fast form in photographic layers, but the precursor compounds may also be of the type which have a certain, although limited capacity for diffusion as complete compounds.

The releasable group Y is generally attached to C through a hetero atom which forms part of the releasable group. Thus, the residue of the photographically active compound may be attached to the carbon atom in general formula I through an oxygen, sulphur, selenium or nitrogen atom or, for example, through an SO$_2$ group. The photographically-active compound may be, for example, a dye, a coupler coupling with or without the formation of colour, a hardener, a silver halide solvent, a fogging agent, a development accelerator or inhibitor, a developer compound, a bleaching inhibitor or accelerator, a mordant or a sensitizer. The most important examples of photographically-active compounds are development inhibitors, such as derivatives of benzotriazole or heterocyclic mercapto compounds, in particular 1-phenyl-5-mercaptotetrazole (PMT) and derivatives thereof.

Y may be the residue of a photographically-active compound or the residue of a precursor compound thereof. It constitutes such a precursor compound if the photographically-active compound is initially released in a masked form when the bond between Y and C is broken and only becomes active when the masking group is removed under the conditions of photographic development. Thus, for example, an additional time control member may be arranged between the time control member according to the present invention and the residue of the photographically-active compound. In that case, the photographically-active compound becomes active as a result of the following sequence of events:

(1) Coupling and release of the coupler residue from the time control member according to the present invention, (2) release of the time control member according to the present invention from the additional time control member, and (3) release of the additional time control member from the photographically-active compound.

Y may also represent the residue of a photographically-inactive compound, when the compounds of the present invention are true 2-equivalent couplers. Examples of such photographically-inactive compounds are aliphatic alcohols, phenoles or nitrogen-containing, preferably heterocyclic compounds as are known as leaving groups in the chemistry of 2-equivalent color couplers.

A is this case represents the residue of a cyan, magenta or yellow color coupler.

The group R is important in two respects for activating the photographically-active compound. Firstly, by virtue of its size it has an important influence on the speed of diffusion of the primary product:

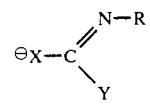

released from the coupler. Secondly, mainly due to its influence on the distribution of electrons within this group, it influences the speed with which Y$^-$ and hence the photographically-active compound becomes available and active. The group R thus determines the average distant between the point at which the photographically-active compound unfolds its activity and the spot at which the precursor compound was situated. R preferably represents a substituted phenyl group, and the time delay of release of Y may be influenced as desired by varying the substitution on the phenyl ring.

The alkyl group mentioned in the definition of R, R$^1$ and R$^2$ may be straight- or branched-chain and preferably contains not more than 8 carbon atoms. An aralkyl group mentioned in the definition of R may be, for example, benzyl or phenethyl.

An aryl group mentioned in the definition of R, R$^1$ and R$^2$ is preferably phenyl which may be substituted, e.g. with halogen, nitro —CF$_3$, alkoxy, acylamino, sulphamoyl or carbamoyl.

An acyl group as referred to herein is obtained by removal of a hydroxyl group from organic carboxylic or sulphonic acids or from carbonic acid monoesters or carbamic or sulphamic acids.

A heterocyclic group may be, for example, a benzoxazolyl, a benzotriazolyl or triazinyl group.

Examples of precursor compounds according to the present invention are shown below:

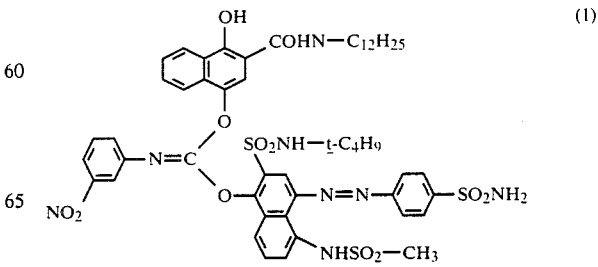

-continued
(2)
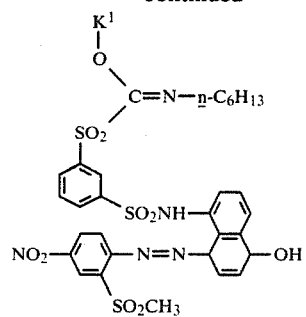
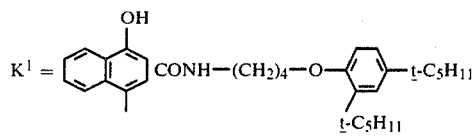
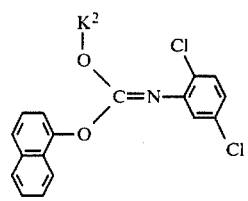
(3)
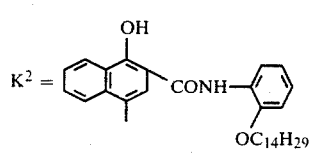
(4)
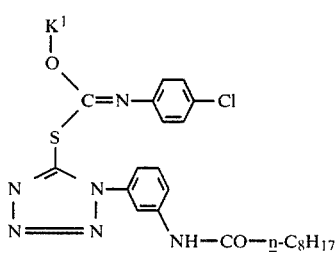
(5)
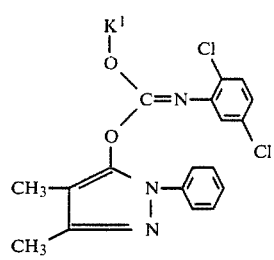
(6)
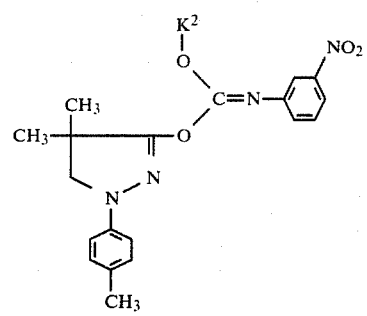
-continued
(7)
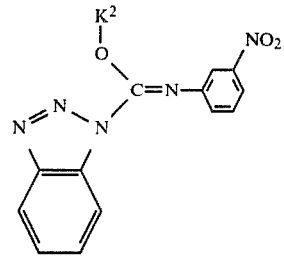
(8)
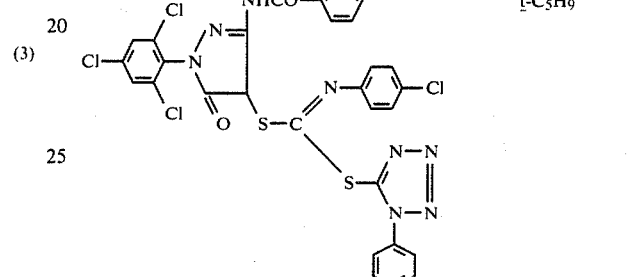
(9)
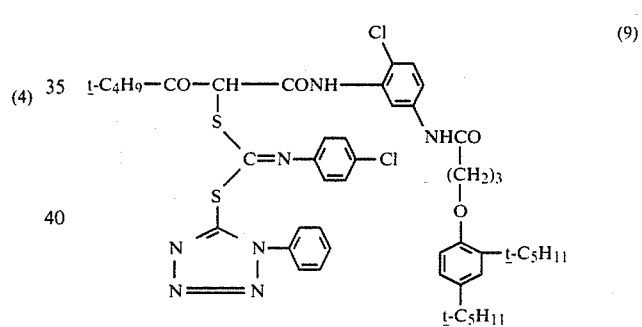
(10)
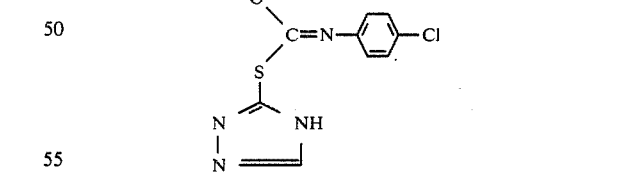
(11)
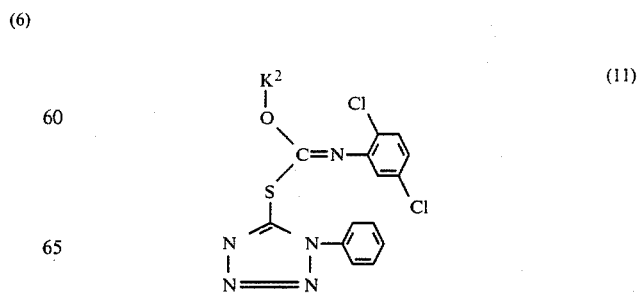

(12)
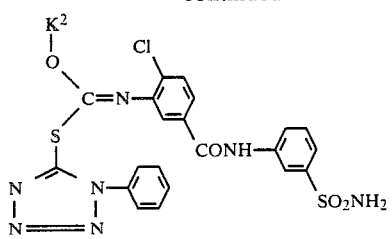

(13)
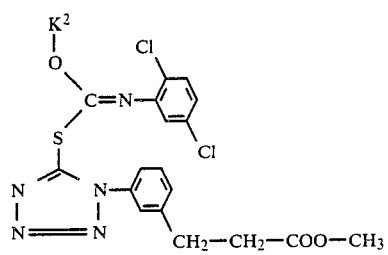

(14)
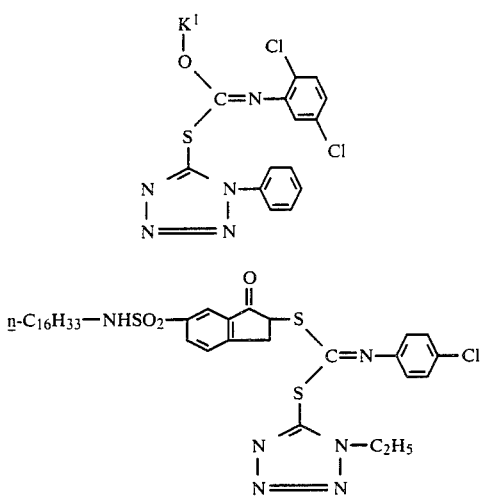

(15)

n-C₁₆H₃₃—NHSO₂—

(16)
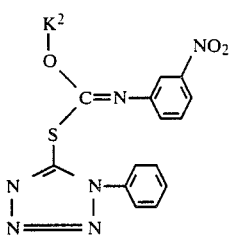

(17)
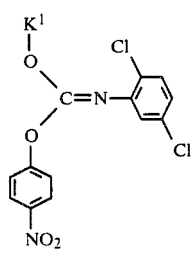

Release of the residue bonded to the coupling position of A and, as the case may be, release of the photographically-active compound is presumably produced by the following reaction sequence:

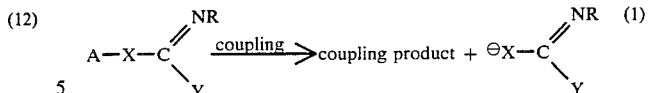

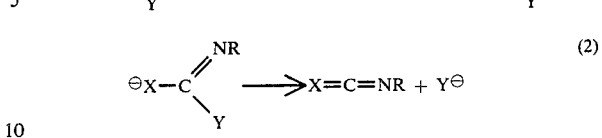

The primary product

is split off in the first step and then decomposes under the conditions of photographic development to release the photographically-active compound, possibly in the form of a precursor compound which is unstable under alkaline conditions. This unstable precursor compound must be distinguished from the precursor compounds which constitute the subject of the present invention. The latter are not unstable under alkaline conditions and they require the presence of oxidized silver halide developer for releasing the photographically-active compounds.

Particularly preferred are those compounds corresponding to general formula I which release a development inhibitor as photographically-active compound. Depending upon the length of life and the diffusibility of the primary product released from the compounds according to the present invention, a controlled diffusion of the inhibitor is achieved within a certain region around the point at which the coupling and hence release of the primary product take place. As is well known, such controlled diffusion of the inhibitor exerts an important influence on the edge effect and hence on the sharpness of photographic recording materials [Phot. Sci. and Eng. 15, 82, (1971), and 18, 131, (1974)].

Various methods are available in the art for the production of the precursor compounds according to the present invention.

Method A:

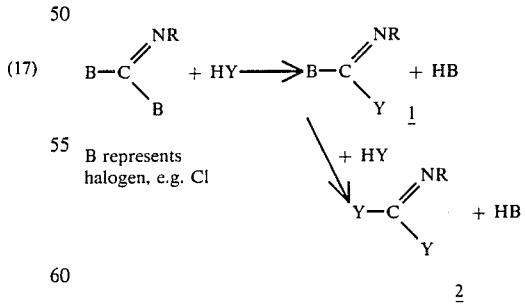

B represents halogen, e.g. Cl $\underline{1}$ or $\underline{2}$ + A—XH ⟶ I + HB ( or HY)

$\underline{3}$

Method B: (for X = O or S; Y = SR')

-continued

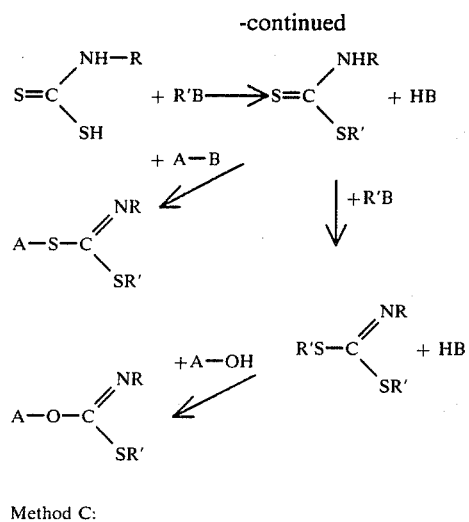

Method C:

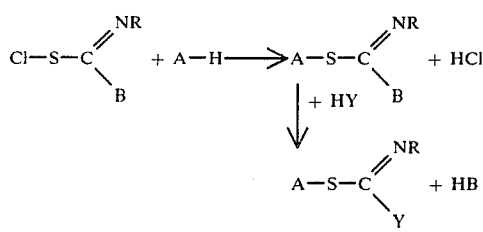

Method D:

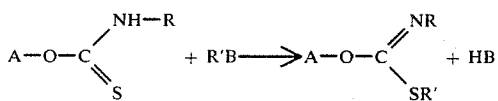

Method E:

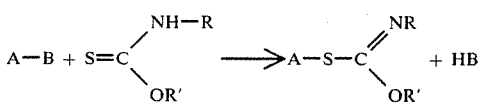

The reactions illustrated above and the compounds used for them are known from the literature e.g.

Method A: Angew. Chem. 81, 18, (1969); Synthesis 1982, 984; Synthesis 1971, 575; Chem. Ber. 99, 239, (1966).

Method B: J. Med. Chem. 25, 557, (1982); Chem. Ber. 99, 239, (1966).

Method C: Synthesis 1970, 561, 575; J. Amer. Chem. Soc. 77, 5171, (1955); Angew. Chem. 77, 427, (1965).

Method D: J. Amer. Chem. Soc. 77, 581.

Compounds of formula A-OH have been described, for example, in No. DE-A-2,590,408, U.S. Pat. No. 3,419,391 and U.S. Pat. No. 3,408,194.

The production of Compound 11 is illustrated below.

Production of Compound 11

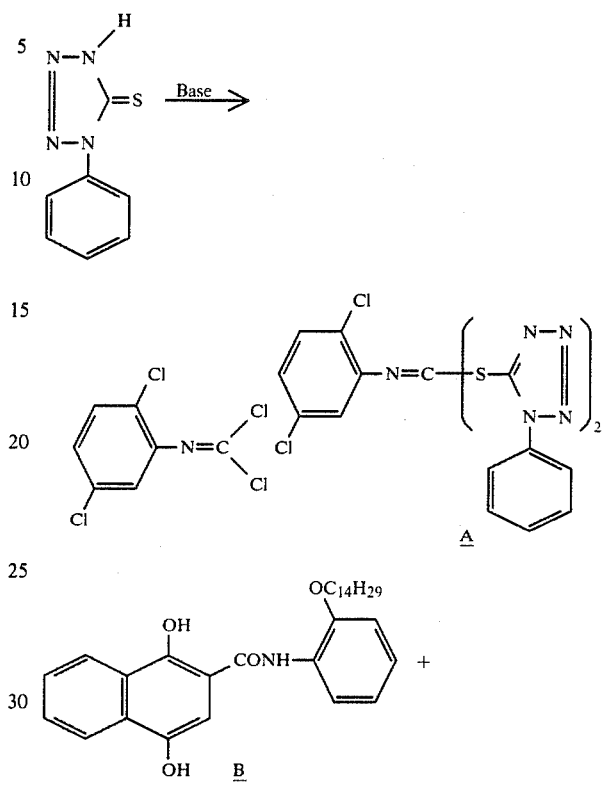

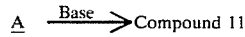

Compound A (Intermediate Product)

12 g of 2,5-dichlorophenyl isocyanide dichloride and 14 ml of triethylamine are added successively with stirring to 17.8 g of 1-phenyl-5-mercaptotetrazole suspended in 100 ml of acetonitrile.

80 ml of water are added dropwise after one hour.

The precipitate is collected and washed with water and then with methanol. 25 g of Compound A, decomposing at 163° C. are obtained.

Compound 11

2 ml of triethylamine are added to a suspension of 5 g of 1,4-dihydroxy-2'-n-tetradecyloxy-2-naphthanilide (Compound B) and 5.2 g of Compound A in 50 ml of acetonitrile under halogen with stirring, and the reaction mixture is heated to 55° C. for 4 hours. After the reaction mixture has been left to stand overnight at room temperature, 160 ml of methanol containing 2 ml of glacial acetic acid are added with stirring. The mixture is stirred for one more hour on an ice bath and the precipitate formed is suction filtered and washed with methanol.

The precipitate is suspended in 100 ml of methanol and the suspension is stirred for 0.5 hour near its boiling point. After the suspension has been left to cool, finally on an ice bath, 6.9 g (79% of the theoretical yield) of Compound 11 melting at 102°–103° C. are obtained after suction filtration and drying.

|   | Calculated [%] | Observed [%] |
|---|---|---|
| C | 64.35 | 64.1 |
| H | 5.8 | 5.7 |
| N | 10.0 | 9.8 |

Compound 7 is obtained by an analogous procedure:

|   | Calculated [%] | m.p. 100° C.<br>Observed [%] |
|---|---|---|
| C | 69.9 | 69.5 |
| H | 6.4 | 6.6 |
| N | 11.1 | 11.1 |

The precursor compounds according to the present invention may be used in conventional recording materials containing silver halide, where they have an advantageous effect on the photographic properties. In colour photographic materials, particularly those developed by the chromogenic process, the effects particularly to be mentioned are the marked improvement in the relationship between sensitivity and colour graininess and the improved sharpness and colour reproduction which are due to the edge effects and inter-image effects achieved when compounds releasing a development inhibitor are used according to the present invention.

The precursor compound according to the present invention is present in at least one layer of the photographic recording material, preferably in a light-sensitive silver halide emulsion layer. The concentration at which the precursor compound according to the present invention is used may vary within wide limits according to the purpose for which it is used; for example, compounds releasing an inhibitor may be used in a silver halide layer in quantities of from $2 \times 10^{-6}$ to $2 \times 10^{-2}$ mol per mol of silver halide. The most suitable concentration may easily be determined by a routine test series. The precursor compounds according to the present invention are incorporated in the photographic layers by the conventional methods (advantageously from solutions in organic solvents or in the form of emulsions).

The effect of the photographically-active compounds released from the precursor compounds according to the present invention may be produced both in the layer in which the precursor compounds are incorporated and in adjacent layers into which the primary product or the photographically-active compound released therefrom may diffuse. The precursor compounds according to the present invention are thus able to exert various controlling actions on the processes taking place in the various layers during development, and the vicinal effects made possible by means of the compounds according to the present invention are also able to influence the development of one silver halide emulsion layer by the results of imagewise development in another layer so that an overall improvement in colour graininess, sharpness and colour reproduction may be achieved. The use of the precursor compounds according to the present invention in partial layers of a partial colour unit consisting of several partial layers of the same spectral sensitivity is also of interest. Such partial layers are not necessarily arranged directly one above the other in the photographic material, but may be separated by other layers, e.g. by a partial layer of a partial colour unit having a different spectral sensitivity.

Layers differing in spectral sensitivity are as a rule separated by light-insensitive intermediate layers in order to prevent unwanted diffusion of developer oxidation products into layers which contain colour couplers but are not (spectrally) associated. These intermediate layers may be layers of pure binder or layers of binder containing additives, such as compounds capable of reacting with diffusible developer oxidation products, or filter dyes, hardeners, developers or UV absorbents.

Where colour couplers are present in the photographic recording material according to the present invention, these are generally of the type which may be incorporated in photographic casting solutions by means of oil-formers. Such couplers are generally soluble in organic solvents, in particular in oil-formers (so-called "hydrophobic couplers"), although hydrophilic couplers may also be used. The couplers are 2-, 4- or 6-equivalent colour couplers (Research Disclosure 19536—July 1980). They may be colourless or coloured masking couplers) and normally contain a ballast group, preferably in a non-coupling position, to enable them to be fixed in a diffusion-fast form in their particular layer. Various image dyes are obtained therefrom in the process of chromogenic development. Other couplers may be used in addition, e.g. white couplers or couplers releasing a photographically-active groups in imagewise distribution.

For the development of the photographic recording materials according to the present invention, it is preferred to use developers of the type conventionally used for chromogenic development. Examples include the known p-phenylene diamine derivatives, such as
N,N-dimethyl-p-phenylene diamine,
N,N-diethyl-p-phenylene diamine,
monomethyl-p-phenylene diamine,
2-amino-5-diethylaminotoluene,
N-butyl-N-(O-sulphobutyl-p-phenylene diamine,
2-amino-5-(N-ethyl-N-$\beta$-methane-sulphonamidoe-
thylamino)-toluene,
N-ethyl-N-$\beta$-hydroxyethyl-p-phenylene diamine,
N,N-bis-($\beta$-hydroxyethyl)-p-phenylene diamine,
2-amino-5-(N-ethyl-N-$\beta$-hydroxyethylamino)-toluene,
and the like.

Other suitable colour developers have been described, for example, in J. Amer. Chem. Soc. 73, 3100 (1951).

Suitable choice of a silver halide developer compound for releasing the photographically-active compound from the precursor compound according to the present invention depends mainly on the ability of the silver halide developer compound to undergo oxidative coupling with the precursor compound. The quality of the dye produced from the precursor compound is of only minor importance. It is therefore also suitable to use silver halide developer compounds which either do not form stable dyes in the coupling reaction or produce dyes which do not have optimum colour properties.

EXAMPLE 1

One of the DIR couplers shown in Table 1 below was added to 500 ml of a sulphur and gold ripened, red-sensitized silver iodobromide emulsion (6 mol-% iodide, average grain diameter 0.65 $\mu$m) which contained per kg the quantity of silver halide equivalent to 200 g of AgNO$_3$ and 50 g of gelatine and had been stabilized with 1 g of 4-hydroxy-6-methyl-1,3,3a,7-tetraazaindene, and the emulsion was then mixed with a colour coupler emulsion of 25 g of colour coupler corresponding to the followiwng formula:

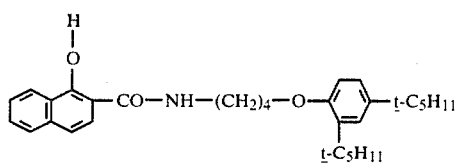

25 g of tricresyl phosphate and 25 g of gelatine.

The DIR coupler, the tricresyl phosphate and gelatine were emulsified in proportions, by weight, of 1:1:1. $3 \times 10^{-3}$ mol of the DIR coupler were added in each case to 1 mol of silver halide.

A blank sample (emulsion+colour coupler emulsion) was prepared by the same method, but without the addition of DIR coupler.

The casting solutions obtained were cast on layer supports (silver application 2.0 g/m²) and hardened to produce materials 1 to 6 (see Table 1).

The magnitude of the "edge effect" was determined by X-ray (to avoid light scattering) as described in T. H. James, The Theory of the Photographic Process, 4th Edition, Macmillan Publishing Co. Inc. New York/London (1977), pages 609–614. Both a macro field and a strip 30 μm in width of each sample were exposed to the same dose of X-ray. The samples were then processed by a colour negative process described in "The British Journal of Photography", 1974, pages 597 and 598. The density difference between the strip (micro density) and the macro field (macro density) measured on these samples at that X-ray dose at which the macro density=1.0 serves as measure of the edge effect in Table 1.

TABLE 1

| Material | DIR coupler | Edge effect at macro density = 1 cyan |
|---|---|---|
| 1 | — | 0.05 |
| 2 | A | 0.32 |
| 3 | B | 0.42 |
| 4 | 11 | 0.52 |
| 5 | 14 | 0.50 |
| 6 | 16 | 0.49 |

EXAMPLE 2

A colour photographic colour negative recording material (Material 7) was produced by applying the layers indicated below in the sequence given to a transparent layer support of cellulose triacetate. The quantities are based in each case on 1 m². The quantities of silver halide applied are given in the corresponding quantities of AgNO₃.

Layer 1 (Antihalation layer). Black colloidal silver sol containing 1.5 g of gelatine and 0.33 g of Ag.
Layer 2 (Intermediate layer). 0.6 g of gelatine.
Layer 3 (1st red-sensitized layer). Red-sensitized silver iodobromide emulsion (5.5 mol-% iodide; average grain diameter 0.45 μm) containing 3.8 g of AgNO₃, 2.5 g of gelatine, 0.9 g of cyan coupler corresponding to the following formula:

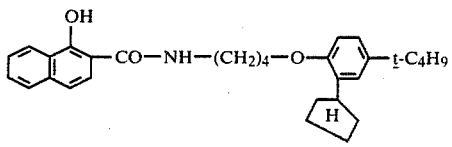

and 0.1 g of masking coupler corresponding to the following formula:

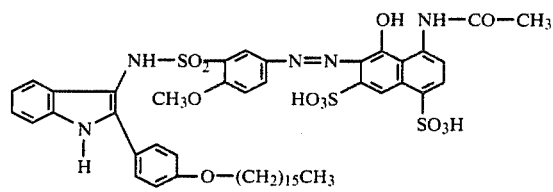

Layer 4 (2nd red-sensitive layer). Red-sensitized silver iodobromide emulsion (6.5 mol-% iodide; average grain diameter 0.8 μm) containing 3.0 g of AgNO₃, 2.0 g of gelatine and 0.2 g of the cyan coupler contained in layer 3.
Layer 5 (Intermediate layer). 0.7 g of gelatine and 0.2 g of diisooctylhydroquinone.
Layer 6 (1st green-sensitized layer). Green-sensitized silver iodobromide emulsion (4.8 mol-% iodide; average grain diameter 0.40 μm) containing 3.0 g of AgNO₃, 2.4 g of gelatine and 0.9 g of magenta coupler corresponding to the following formula:

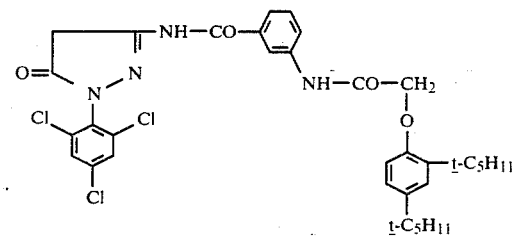

0.09 g of DIR coupler corresponding to the formula

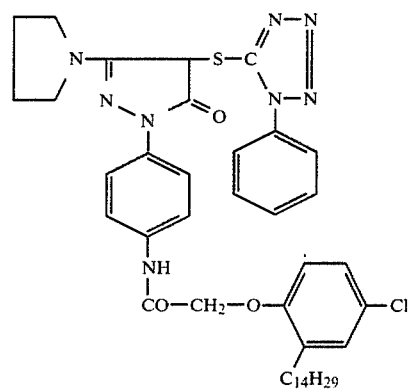

and 0.1 g of masking coupler corresponding to the formula:

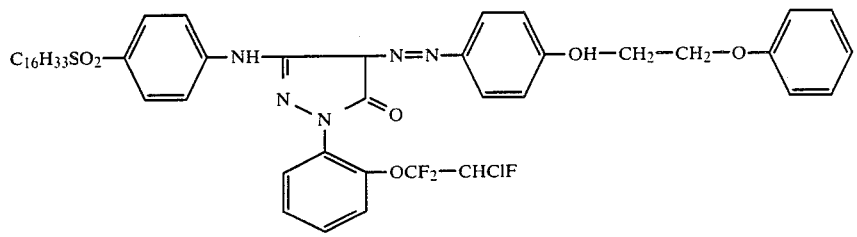

Layer 7 (2nd green-sensitized layer). Green-sensitized silver iodobromide emulsion (4.3 mol-% iodide; average grain diameter 0.70 μm) containing 2.5 g of AgNO₃, 1.6 g of gelatine and 0.21 g of the magenta coupler contained in layer 6, as well as 0.02 g of the masking coupler contained in layer 6.

Layer 8 (Intermediate layer). 0.5 g of gelatine and 0.15 g of 2,5-diisooctylhydroquinone.

Layer 9 (Yellow filter layer). Yellow colloidal silver sol containing 0.2 g of Ag and 0.9 g of gelatine.

Layer 10 (1st blue-sensitive layer). Blue-sensitized silver iodobromide emulsion (4.9 mol-% iodide; average grain diameter 0.45 μm) containing 0.76 g of AgNO₃, 0.85 g of gelatine and 1.35 g of yellow coupler corresponding to the following formula:

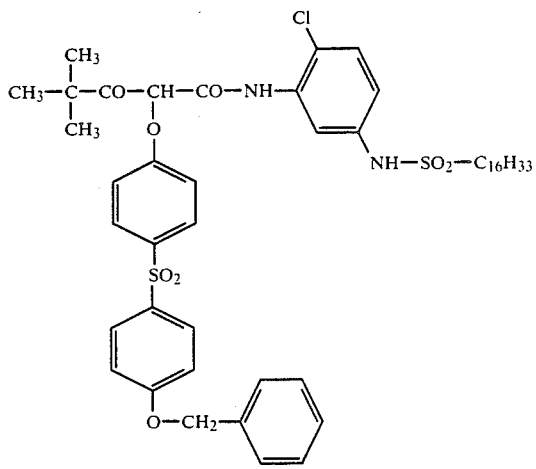

Layer 11 (2nd blue-sensitive layer). Blue-sensitized silver iodobromide emulsion (3.3 mol-% iodide; average grain diameter 0.85 μm) containing 1.0 g of AgNO₃, 0.85 g of gelatine and 0.5 g of the yellow coupler contained in layer 10.

Layer 12 (Protective layer). 1.2 g of gelatine.

Layer 13 (Hardening layer). 1.5 g of gelatine and 0.7 g of hardener corresponding to the following formula:

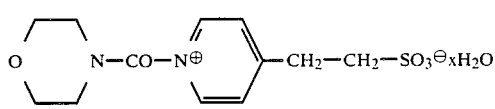

All silver halide emulsions of this material had been stabilised with 0.5 g of 4-hydroxy-6-methyl-1,3,3a,7-tetraazaindene per 100 g of AgNO₃.

Materials 8 to 12 were prepared by analogous methods, but layer 3 in addition contained 0.11 mmol of one of the DIR couplers indicated in Table 2 below.

The magnitude of the edge effects was determined on materials 7 to 12 by the metod described in Example 1. Table 2 shows that the DIR couplers according to the present invention incorporated in layer 3 produce higher edge effects not only in the cyan, but also (obviously due to vertical vicinal effects) in the magenta.

The sharpness of materials 7 to 12 was determined by means of the modulation transfer function (MTF). The method is described in T. H. James, The Theory of the Photographic Process, 4th Edition, Macmillan Publishing Co. Inc. New York/London (1977), page 605.

In Table 2 are quoted those local frequencies (in lines per mm) for materials 7 to 12 at which the MTF is 50%. The higher MTF values obtained with the DIR couplers according to the present invention show that these couplers give rise to a sharper image.

The inter-image effect which improves the colour quality from cyan to magenta is also enhanced by the DIR couplers according to the present invention. The "Magenta Inter-image Effect" ($IIE_{mg}$) is given in Table 2 in terms of the percent by which the magenta gradation is higher on exposure to green light than on exposure to white light.

For determining the edge effect, the MTF and the inter-image effect, the materials indicated in this Example are processed by the same colour negative process as in Example 1.

TABLE 2

| Material | DIR coupler | $IIE_{mg}$ [%] | Edge effect at macrodensity = 1 | | MTF = 50% lines/mm | |
|---|---|---|---|---|---|---|
| | | | cyan | magenta | cyan | magenta |
| 7 | — | −15 | 0.15 | 0.10 | 20 | 32 |
| 8 | A | +10 | 0.35 | 0.26 | 24 | 35 |
| 9 | B | +20 | 0.40 | 0.30 | 28 | 38 |
| 10 | 11 | +25 | 0.48 | 0.35 | 31 | 40 |
| 11 | 14 | +25 | 0.48 | 0.34 | 30 | 38 |
| 12 | 16 | +20 | 0.45 | 0.34 | 29 | 38 |

The following DIR couplers, which are not according to the present invention, were used for comparison (in materials 2, 3, 8 and 9)

DIR coupler A

-continued

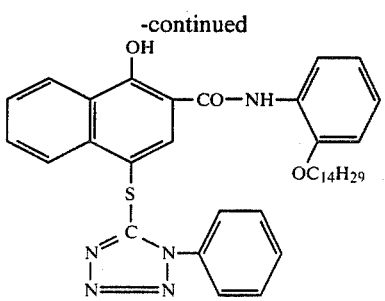

DIR coupler B

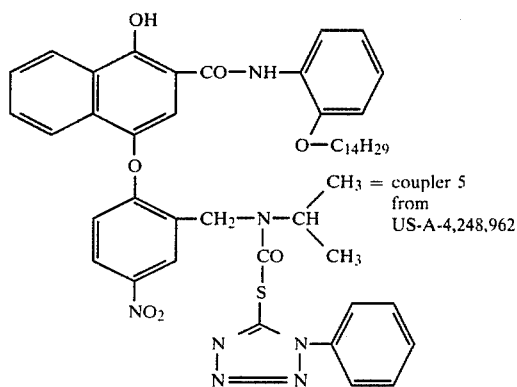

CH₃ = coupler 5 from US-A-4,248,962

We claim:

1. Photographic recording material having at least one silver halide emulsion layer, characterised by containing a compound corresponding to the following general formula I:

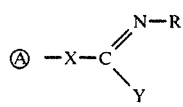

wherein

A represents the residue of a compound which is capable of oxidative coupling with a silver halide developer compound under the conditions of photographic development and having the group

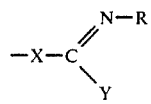

bonded to its coupling position;

X represents —O—, —S— or —NR¹—;

Y represents a releasable group attached to C through a heteroatom which forms part of the releasable group and capable of being released together with said heteroatom from C as a function of photographic development, taking with it the bonding electron pair between C and Y, when X is released from A, taking with it the bonding electron pair between A and X; said releasable group being the residue of a photographically active compound or the residue of an alkali-labile precursor of a photographically active compound R represents alkyl, aralkyl, aryl, acyl, a heterocyclic group, or a group —NH—acyl, —OR² or —P(O)(OR²)₂;

R¹ represents H, alkyl, aryl, alkylsulphonyl or arylsulphonyl; and

R² represents alkyl, aryl or a heterocyclic group.

2. Recording material as claimed in claim 1 wherein in general formula I the releasable group Y is attached to the carbon atom by an oxygen, sulphur or nitrogen atom.

3. Recording material as claimed in claim 1 wherein in general formula I R represents a phenyl ring which may be substituted with halogen, nitro, CF₃, alkoxy, acylamino, sulphamoyl and/or carbamoyl.

4. Recording material as claimed in claim 1 wherein Y represents the residue of a development inhibitor.

* * * * *